United States Patent [19]
Kühn et al.

[11] Patent Number: 4,553,087
[45] Date of Patent: Nov. 12, 1985

[54] METHOD AND APPARATUS FOR DETERMINING THE PENETRATION AND LEACHING PROCESS OF CONDUCTIVE PHASES

[75] Inventors: Wilhelm Kühn; Claus Bunnenberg, both of Hanover, Fed. Rep. of Germany

[73] Assignee: Gesellschaft für Strahlen- und Umweltforschung mbH, München, Neuherberg bei München, Fed. Rep. of Germany

[21] Appl. No.: 393,825

[22] Filed: Jun. 30, 1982

[30] Foreign Application Priority Data
Oct. 7, 1981 [DE] Fed. Rep. of Germany ....... 3139835

[51] Int. Cl.[4] .................. G01N 5/02; G01N 25/56; G01R 27/02
[52] U.S. Cl. .................. 324/65 P; 324/65 R; 73/73
[58] Field of Search .......... 324/65 P, 65 R, 61 P, 324/376, 355; 73/73; 340/602, 620, 605

[56] References Cited
U.S. PATENT DOCUMENTS

| | | | |
|---|---|---|---|
| 2,183,565 | 12/1939 | Hawley | 324/355 X |
| 2,802,173 | 8/1957 | Nisle | 324/376 |
| 4,341,112 | 7/1982 | Mackay | 73/73 |

FOREIGN PATENT DOCUMENTS
180405 8/1966 U.S.S.R. ................ 73/73

Primary Examiner—Stanley T. Krawczewicz
Assistant Examiner—Jose M. Solis
Attorney, Agent, or Firm—Spencer & Frank

[57] ABSTRACT

Method for one-time or continuous nondestructive determination of the penetration and leaching process of conductive phases in materials, wherein the conductivity of the material to be examined is measured in thin superposed layers in that, after applying voltage to pairs of oppositely disposed conductor paths associated with these layers, the current flow through separate layers of the material is measured and an increase of the current in increasingly deep layers indicates the advance of the front of the penetrating phase.

11 Claims, 5 Drawing Figures

METHOD AND APPARATUS FOR DETERMINING THE PENETRATION AND LEACHING PROCESS OF CONDUCTIVE PHASES

BACKGROUND OF THE INVENTION

The present invention relates to method and apparatus for one-time or continuous nondestructive determination of the penetration and leaching process of conductive phases in materials.

The determination of the penetration depth of a liquid phase in porous materials plays an important part, primarily in the so-called water impermeability tests of concrete samples. The only testing method known so far, and defined in DIN-Standard 1048, Part I (German Industrial Standard), for the determination of the penetration depth of water in concrete is based on the splitting of a test body according to defined charging conditions, and visual evaluation of the moisture penetration depth at the break surface. The same method is also employed to examine the penetration and leaching behavior of salt solutions in concrete to test suitable concrete mixtures for the storage of radioactive wastes in salt domes (see, for example, R. Wendehorst, *Baustoffkunde* (Construction Materials), published by C. R. Vincentz Verlag, Hannover 1975, and G. Franz, *Beton Kalendar* (Concrete Calendar) 1980, Part II, published by W. Ernst & Sohn, Berlin, 1980 and Verein Deutsche Zementwerke, *Zement Taschenbuch* [Cement Handbook] 79/80, published by Bauverlag, Wiesbaden, 1980).

This testing method has considerable drawbacks. It harbors a large inaccuracy component which is produced mainly by the visual evaluation of the moisture penetration depth at the split surface of the sample body. This applies particularly in the case of solutions, since the dissolved substance and the solvent exhibit different penetration behaviors. In leaching tests there exists an additional difficulty that visible fronts do not appear at all and slight gradual differences cannot be detected. Moreover, the sample body is destroyed. This necessary splitting of the sample body makes it unusable for further measurements. Continuous measurements and long-term observations, e.g., stability of impregnations and coatings, are therefore impossible. Moreover, discontinuities during the penetration and leaching process cannot be detected. Finally, the regular monitoring of already installed components or instorage concrete shieldings cannot be performed. This is of significance particularly, for example, in the permanent storage of radioactive wastes where under certain circumstances certain changes may take place in the interior of the shielding material.

However, such information has great significance in connection with the storage of radioactive wastes. On the one hand, storage barrels or drums are encased in a concrete shield which, upon storage in a salt dome, may be exposed to a salt solution if there is a water break-in. Additionally, it is necessary, on the one hand, to test concrete mixtures which are highly resistant to the penetration of the solution while, on the other hand, long-term changes in the permeability of the shielding material must be able to be monitored.

Additionally, liquid radioactive wastes are sometimes incorporated in a cement mixture for permanent storage. In such case, the leaching behavior of these substances must be tested and monitored.

In the construction industry as well, knowledge of the transport of moisture and salts in construction materials is of great importance because these factors decisively determine the durability of the material and the setting of a defined microclimate within the enclosed area of the structure. Changes in these properties due to the use of paints and sealers also play a significant role here.

Finally, in road construction, potholes are ascribed primarily to water vapor which in winter rises from lower layers and is condensed and frozen in the upper roadway coating. Efforts are therefore continuing to find materials for the cover layer which are substantially impermeable to water vapor diffusions.

SUMMARY OF THE INVENTION

It is the object of the present invention to be able to examine the penetration and leaching behavior of substances in more or less porous materials, with the momentary properties as well as the long-term behavior of the material itself and of interior and exterior additives (e.g. impregnations, sealers, paints etc.) being included in the examination.

The above object is achieved according to the present invention by a method for one-time or continuous nondestructive determination of the penetration and leaching process of conductive phases in materials, which comprises measuring the conductivity of the material to be examined in thin superposed layers from the penetration surface by:

providing a respective like pattern of conductors on each of two opposite sides of the material to be examined to produce pairs of oppositely disposed conductors with each pair being associated with one of the thin layers; applying a voltage across the pairs of oppositely disposed conductors to cause current to flow between the conductors of each pair through separate layers of the material; and separately measuring the current flowing through each pair of oppositely disposed conductors to determine the current through the individual layers, whereby an increase of the current in increasingly deep layers indicates the advance of the front of the penetrating phase.

According to features of the invention, the applied voltage is an A.C. voltage which is simultaneously applied to each pair of conductors during the current measuring step.

The apparatus according to the invention for carrying out the above method includes first and second like patterns of a plurality of parallel conductive strips of constant width applied to two opposite sides of a body of material to be examined such that each conductor of the first pattern is opposite a conductor of the second pattern to form a respective conductor pair; and circuit means connected to all of the conductors, for simultaneously applying a voltage across each of the conductor pairs, and for separately measuring the current flowing through each conductor pair.

According to features of the invention, the conductors of the conductor patterns may be directly applied to the side surface of the test material, for example, by means of a silver suspension, or may comprise strips of conductive rubber.

In the measuring method according to the invention, the fact is utilized that the electrical conductivity of a material changes with its content of a conductive phase. This refers to the penetration and leaching of conductive substances per se as well as of pure water which more or less dissociates substances existing in the material, and thus changes in the conductivity of the material. The measuring method offers an opportunity for automatically registering and further processing the electrical measured values even over large distances, as is desirable, for example, with radioactive wastes.

DETAILED DESCRIPTION OF THE PREFERRED EMBODIMENTS

Figure 1:
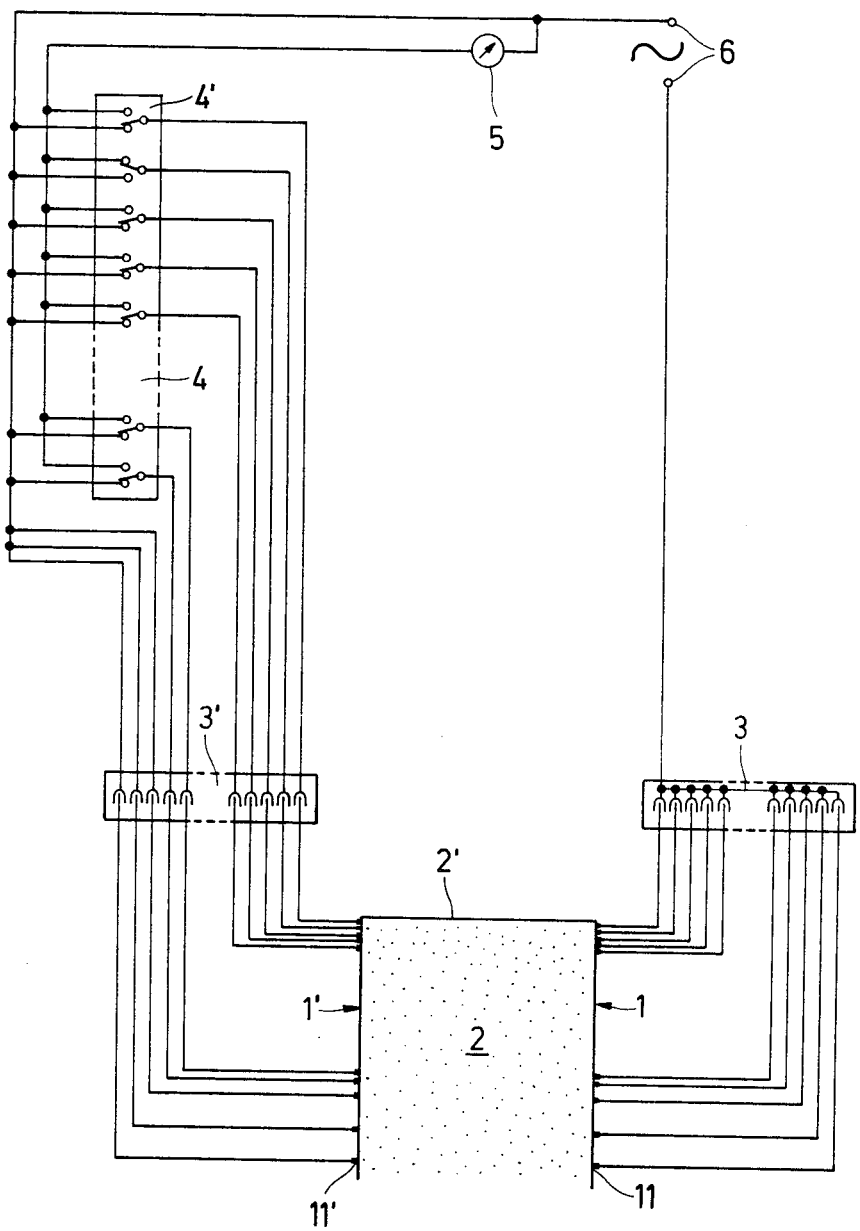
FIG. 1 is the basic circuit diagram for the measuring apparatus according to the invention.

Referring now to FIG. 1, there is shown the basic circuit diagram of the measuring apparatus for measuring the penetration depth of a conductive phase in a sample material 2. The circuit includes conductor patterns 1 and 1' on oppositely disposed side surfaces of material 2 with each conductor of pattern 1 being disposed opposite a conductor in pattern 1'. As will be explained in greater detail below with regard to FIG. 2, the individual conductors of patterns 1 and 1' are narrow and of constant width, and extend parallel to one another in the respective patterns and to the penetration surface 2' of the material 2. The individual conductors, e.g. 40 conductors, of the conductor pattern 1 on one side surface of the material 2 to be examined are combined or connected together in a plug 3 and are connected, via a single conductor, with one pole of the alternating current source 6. The individual conductors of the conductor pattern 1' on the opposite surface of the material 2 are connected via a like plug 3' and separate lines, e.g. 40 lines, to a switch arrangement including a separate switch 4' for each measuring conductor. Each switch 4' is a single pole double throw switch which in one position, the down position in FIG. 1, directly connects the respective measuring conductor to the A.C. voltage source 6, and which in the other position, the up position in FIG. 1, connects the respective measuring conductor to the source 6 via a current measuring device 5.

During the measuring process using the apparatus of FIG. 1, the voltage source 6 is simultaneously applied across all conductor pairs in patterns 1 and 1' and consequently current flows simultaneously through all layers of the material 2. With the aid of the individual switches 4' in the switch arrangement 4, the current measuring device 5 is switched successively into the individual circuits so that the current through each individual layer of material 2 can be determined separately. In the embodiment of FIG. 1, the current is being measured in the second circuit from the top. The voltage of source 6 and the number of conductor paths can be adapted to the particular measuring task. As schematically shown in FIG. 1, and in greater detail in FIG. 2, additional, broader conductor path pairs 11, 11' are disposed below the measuring volume defined by the two opposing conductor path patterns 1 and 1'. These broader conductive path pairs 11, 11' are simply connected across the voltage source 6 and serve to homogenize the electrical field in the material 2.

In the apparatus employed to implement the invention, the penetration or leaching of the conductive phase is determined by measuring the conductivity of the material to be examined in thin, superposed layers. Upon the application of voltage to the pairs of oppositely disposed conductor paths of the conductor patterns 1, and 1', the current to be measured flows in separate layers through the material 2. The increase of current in increasingly deeper layers indicates, for example, the advance of the penetrating conductive phase.

Figure 2:
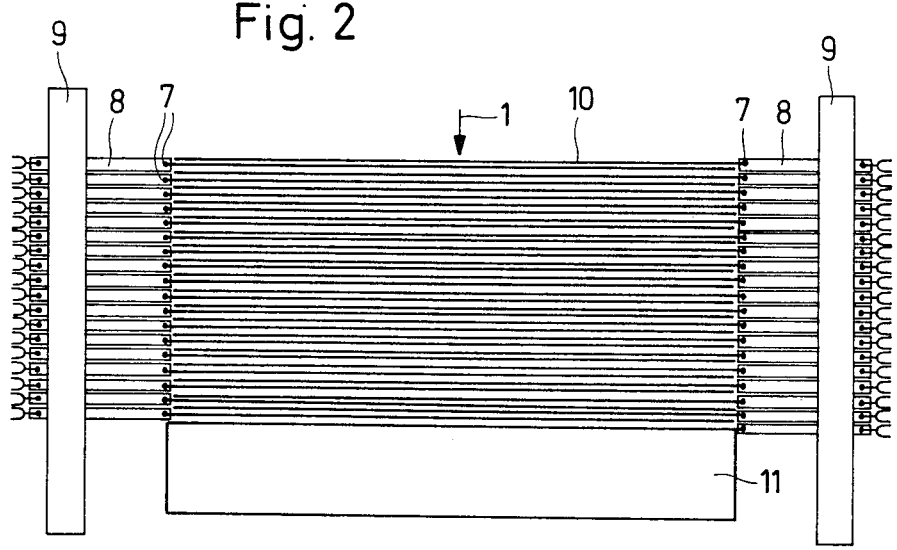
FIG. 2 is a plan view showing a preferred arrangement for the conductor pattern on the material to be measured with the apparatus of FIG. 1.

The current is caused to flow through separate layer by using a conductor pattern as shown, for example, in FIG. 2. Each conductor pattern 1 or 1' includes a plurality of parallel narrow conductors or conductive paths 10 of constant width, and preferably with a constant spacing. As shown, the conductors 10 are parallel to the surface 2' through which the penetration to be measured takes place. One end of each of the conductors 10 is provided with a circular broadened portion 7 which serve as contact points for spring contacts 8 which are in turn mechanically fastened to a plate or insulator 9 in an electrically separated manner. Preferably, as shown and in order to save space and permit easier contacting of the narrow conductors 10, the contacting alternates from one end of a conductor 10 to the other end of the adjacent conductor 10.

The pattern of the conductors shown in FIG. 2 is applied to the side surfaces of material to be tested. This is possible in two advantageous ways:

1. The conductor patterns 1 and 1' may be formed by the direct application of a silver suspension to two oppositely disposed sides of the material 2 (see FIG. 1), for example according to the conductor pattern shown in FIG. 2. Depending on the surface consistency of the test material 2, the silver suspension is applied so as to form strips 10 of a constant width by means of a hollow needle, or it is sprayed on over a strip-shaped template.

2. The conductor patterns 1 and 1' may be formed using conductor paths 10 of a conductive rubber mixture. The conductive rubber conductor paths 10 are then glued onto an insulating backing plate according to the pattern of FIG. 2 and are each provided with electrical terminals 7, 8. The pattern of conductors 1 or 1' is then brought into contact with the side surface of the material 2 and secured in place. The flexibility of the rubber mixture compensates unevennesses in the surfaces of the material so that electrical contact with the material is assured.

Figure 3:
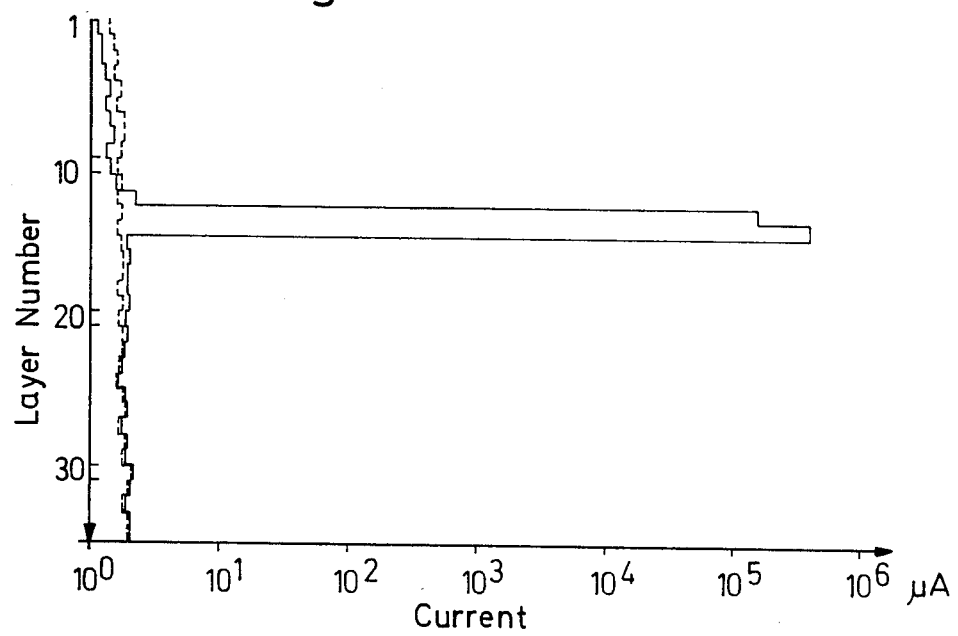
FIG. 3 is a plot of the current profile, resulting from measurements by the apparatus of FIGS. 1 and 2, of a sample of packed loess before (dashed line) and after (solid line) introduction of a layer of highly conductive powder using the apparatus of FIGS. 1 and 2.

In one embodiment of the invention, the conductor paths 10 have a width of 1 mm with a mutual spacing of 1 mm therebetween. This produces a spatial resolution of 2 mm. To check the spatial resolution capability, the current profile in a sample of packed loess was measured, both before and after introduction of a layer of highly conductive carbon powder, by means of the apparatus according to the invention as shown in FIGS. 1 and 2 with the conductors being applied according to alternative 2 above. These measured current profiles are plotted in FIG. 3 which is a plot of the current with respect to the number of the measured layer. As can clearly be seen in FIG. 3, sharp interfaces are visible between the two materials of different conductivity. Moreover, there is no electrical influence between the measuring circuits, so that an actual resolution of 2 mm is assured.

In a further example, the pattern of conductors 10 of FIG. 2 was applied by means of a silver suspension to two oppositely disposed sides of a lime sand brick sample material 2. At various times (t=20 to 420 minutes) after charging the brick with distilled water, the current profiles shown schematically in FIG. 4 were recorded (current through 2 mm layer ($\mu$A); source voltage 18 V). The points of intersection of the current profiles with the current average of the air-dry material, i.e., the line in the hatched region, mark the penetration depth (in mm) of the moisture front.

Figure 4:
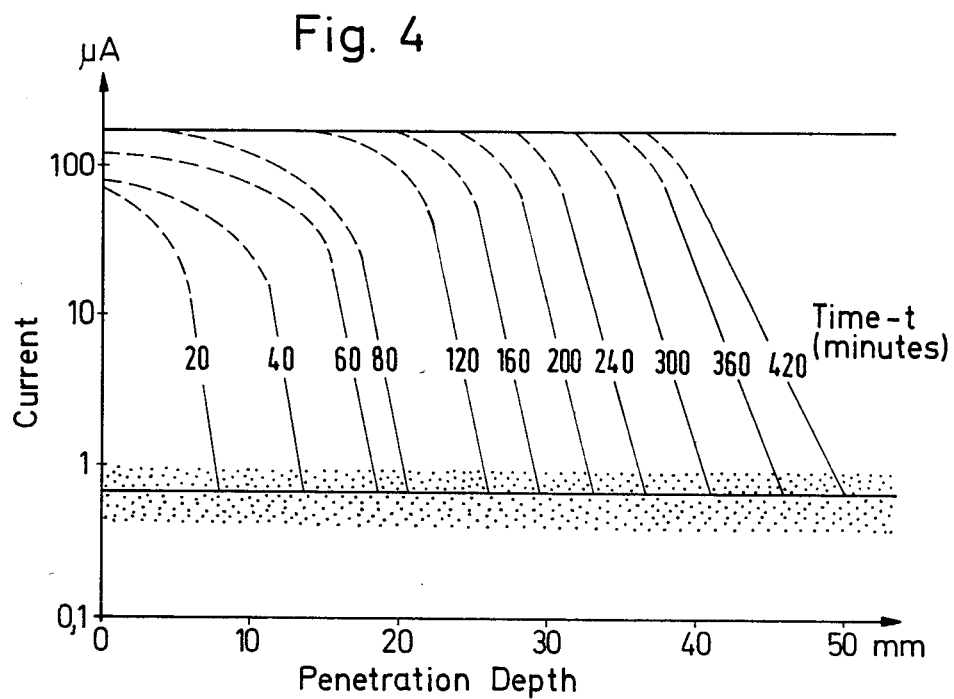
FIG. 4 shows a group of curves of current versus penetration depth at various times, which curves were derived by the method and apparatus according to the invention.
Figure 5:
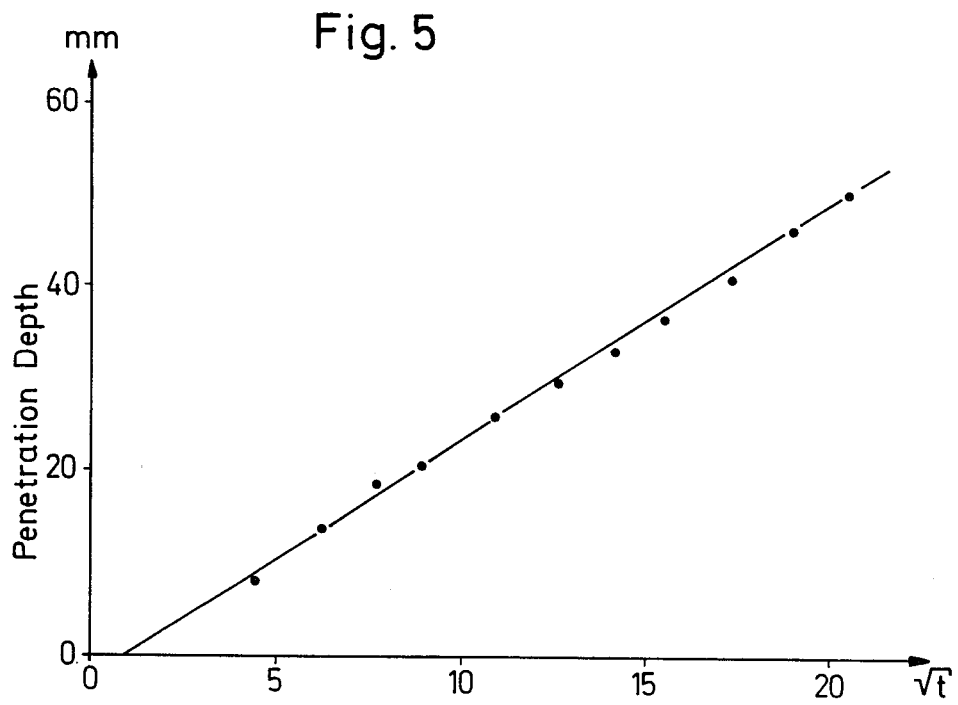
FIG. 5 is a plot of penetration depth versus the square root of the time of measurement of the current profile curves of FIG. 4.

FIG. 5 shows the base points of the current profiles of FIG. 4 in dependence on the square root of the time after charging with respect to the depth of the moisture front in mm.

As to be expected according to the diffusion equations customary in geological physics, the penetration depths measured at various times t fulfill a $\sqrt{t}$ relationship (D. R. Nielsen, R. D. Jackson, J. W. Cary, D. D. Evans (Editors), *Soil Water*, Soil Science Society of America, Madison, Wisc. 1972).

The construction of the conductor paths 10 of FIG. 2 of an Ag suspension is particularly well suited for solid sample bodies. Although such conductor paths 10 must be considered as a lost component of the measuring device when the measuring volume thus produced is incorporated or permanently stored, such a component construction permits, in an advantageous manner, any desired retesting with respect to long-time changes of the material at a later date and at the same location. The construction of the conductor paths 10 of a conductive rubber mixture, on the other hand, is suitable for solid as well as powdered sample materials.

It will be understood that the above description of the present invention is susceptible to various modifications, changes and adaptations, and the same are intended to be comprehended within the meaning and range of equivalents of the appended claims.

What is claimed is:

1. Method for the nondestructive determination of the penetration and leaching process of conductive phases in materials, comprising measuring the conductivity of the material to be examined in thin superposed layers from the penetration surface by:

providing a respective pattern, of thin parallel conductors on each of two opposite side surfaces of the material to be examined to produce pairs of oppositely disposed conductors with each pair being associated with one of said layers; simultaneously applying a voltage across each of said pairs of oppositely disposed conductors to cause current to flow between the conductors of each pair through separate layers of said material; and separately measuring the current flowing through each pair of oppositely disposed conductors to determine the current through the individual layers, whereby an increase of the current in increasingly deep layers indicates the advance of the penetration front of the conductive phase.

2. The method defined in claim 1 used for the impermeability testing of concrete with respect to water or salt solutions.

3. The method defined in claim 1 wherein said voltage is an A.C. voltage.

4. Apparatus for implementing the method according to claim 1 comprising in combination:

first and second patterns of a plurality of parallel conductive strips of constant width applied to two opposite sides of a body of material to be examined such that each conductive strip of said first pattern is opposite a conductive strip of said second pattern to form a respective conductor pair; and circuit means, connected to all of said conductive strips, for simultaneously applying a voltage across each of said conductor pairs, and for separately measuring the current flowing through each said conductor pair.

5. Apparatus as defined in claim 4 further comprising at least one further conductive strip of a greater width than said conductive strips of said patterns disposed on each said side of said material, each said further conductive strip being parallel to said conductive strips of said patterns, opposite the other of said further conductive strips, and spaced further from the penetration surface of the material than said conductive strips of said patterns; and wherein said circuit means simultaneously applies said voltage across said further conductive strips.

6. Apparatus as defined in claim 4 wherein said parallel conductive strips are made of a silver suspension which is directly applied to the sides of said material.

7. Apparatus as defined in claim 4 wherein said parallel conductive strips are made of a conductive rubber mixture which is disposed on insulating backing plates.

8. Apparatus as defined in claim 6 or 7 wherein each of said conductors has a contact point provided at one of its ends, and said circuit means includes spring contacts which contact said contact points.

9. Apparatus as defined in claim 8 wherein a plurality of said spring contacts are fastened to a common insulator strip.

10. Apparatus as defined in claim 4 wherein said conductors are oriented substantially parallel to the end surface of said material through which penetration takes place.

11. Apparatus as defined in claim 4 wherein said voltage is an A.C. voltage.

* * * * *